United States Patent [19]

Rosenberg

[11] Patent Number: 4,610,663
[45] Date of Patent: Sep. 9, 1986

[54] NEPHROSTOMY CATHETER WITH SIDE CONNECTOR

[75] Inventor: Helmut W. G. Rosenberg, McHenry, Ill.

[73] Assignee: The Kendall Company, Boston, Mass.

[21] Appl. No.: 683,052

[22] Filed: Dec. 18, 1984

[51] Int. Cl.$^4$ .............................................. A61M 25/00
[52] U.S. Cl. ........................................ 604/99; 604/283
[58] Field of Search ................................. 604/99–102, 604/283, 284, 244, 905

[56] References Cited

U.S. PATENT DOCUMENTS

| | | | |
|---|---|---|---|
| 1,089,805 | 3/1914 | Wolf | 604/99 |
| 2,930,377 | 3/1960 | Cowley | 604/103 |
| 3,385,301 | 5/1968 | Harautuneian | 604/99 |
| 3,460,540 | 8/1969 | Gagne | 604/98 |
| 3,825,013 | 6/1974 | Craven | 604/99 |
| 3,833,003 | 9/1974 | Taricco | 604/96 |
| 4,020,849 | 5/1977 | Jackson | 604/99 |
| 4,356,824 | 11/1982 | Vazquez | 604/98 |
| 4,445,896 | 5/1984 | Gianturco | 604/283 |

Primary Examiner—Dalton L. Truluck
Assistant Examiner—Karen L. Kaechele
Attorney, Agent, or Firm—Powell L. Sprunger

[57] ABSTRACT

A nephrostomy catheter comprising, an elongated shaft having a drainage lumen extending through the shaft, an inflation lumen extending through a wall of the shaft, and an opening extending through the wall of the shaft and communicating with the drainage lumen adjacent a proximal end of the shaft. The catheter has an elastic sleeve secured to a distal portion of the shaft in circumferential zones, with the sleeve defining a cavity communicating with the inflation lumen. The catheter has a connector removably received in sealing relationship in the opening with the connector communicating with the drainage lumen, and an inflation valve secured to the proximal end of the shaft. Communication is established between the valve and the inflation lumen to inflate the sleeve.

3 Claims, 10 Drawing Figures

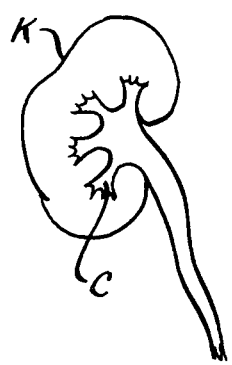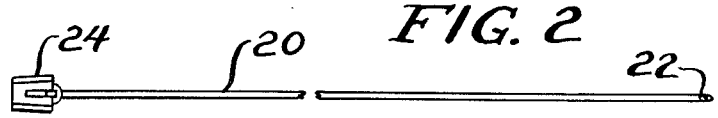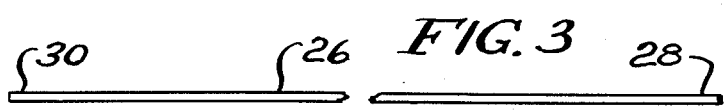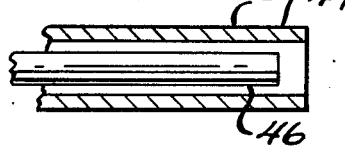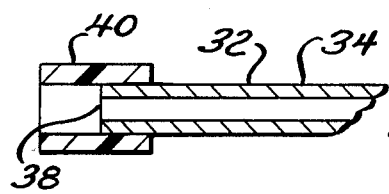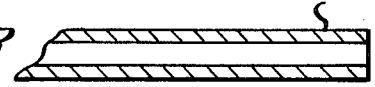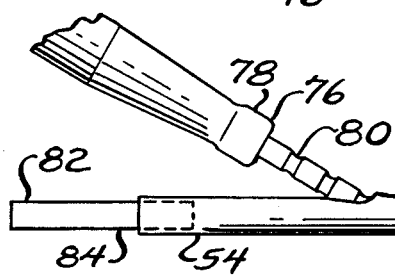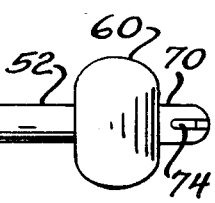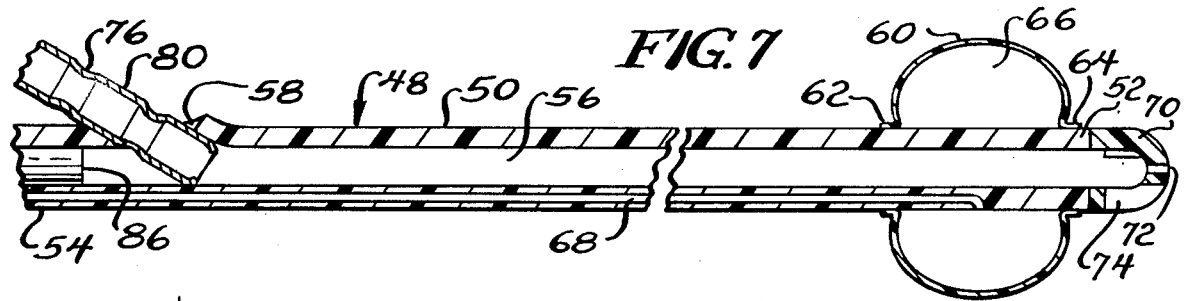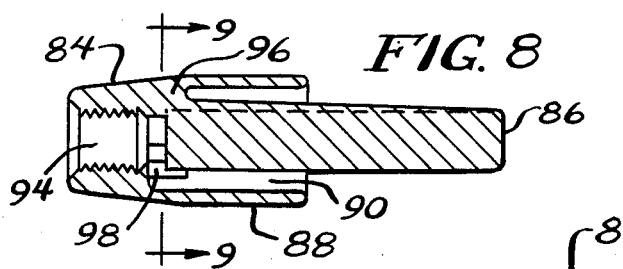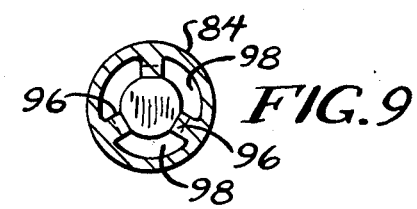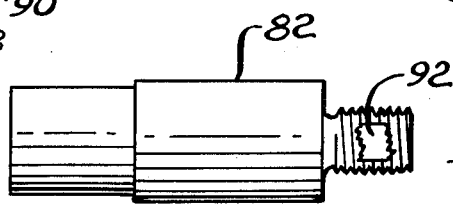

NEPHROSTOMY CATHETER WITH SIDE CONNECTOR

BACKGROUND OF THE INVENTION

The present invention relates to catheters.

When the ureter or kidney of a patient is obstructed by a stone, it is necessary to stabilize the kidney through drainage because an increase of pressure in the kidney could result in loss of the kidney. Such a procedure is called a nephrostomy procedure. First, a small gauge hollow needle is passed under radiologic vision until a tip of the needle is located in the renal calyces to obtain access to the kidney chamber. With the needle in place, a flexible elongated guide wire is passed through the needle, and the needle is removed with the guide wire in place to establish a path to the kidney. Next, a plurality of dilators are inserted over the guide wire in order to increase the size of the path to the kidney, and the dilators are then removed. In the past, a catheter is then placed over the guide wire, with the catheter having a pig tail which is located in the kidney. Although nephrostomy has been completed in this manner, it is desired to improve the procedure.

SUMMARY OF THE INVENTION

A principal feature of the present invention is the provision of an improved nephrostomy catheter.

The catheter of the present invention comprises, an elongated shaft having a drainage lumen extending through the shaft, an inflation lumen extending through a wall of the shaft, and an opening extending through the wall of the shaft and communicating with the drainage lumen adjacent a proximal end of the shaft. The catheter has an elastic sleeve secured to a distal portion of the shaft in circumferential zones, with the sleeve defining a cavity communicating with the inflation lumen.

A feature of the present invention is that the catheter has a connector removably received in sealing relationship in the opening with the connector communicating with the drainage lumen.

Another feature of the invention is that the catheter has an inflation valve secured to the proximal end of the shaft.

Yet another feature of the invention is the provision of means for establishing communication between the valve and the inflation lumen.

A feature of the present invention is that the connector may be removed from the shaft, and a sheath of a scope may be passed over the inflation valve and shaft of the catheter preparatory to viewing the inside of a kidney with an optic telescope.

Further features will become more fully apparent in the following description of the embodiments of this invention and from the appended claims.

DESCRIPTION OF THE DRAWINGS

In the drawings:

FIG. 1 is a diagrammatic view of a kidney of a patient;

FIG. 2 is a fragmentary elevational view of a needle for use in a nephrostomy procedure;

FIG. 3 is a fragmentary elevational view of a guide wire for use in the procedure;

FIG. 4 is a fragmentary elevational view of a stylet for use in the procedure;

FIG. 5 is a fragmentary elevational view of a scope for use during the procedure;

FIG. 6 is a fragmentary elevational view of a catheter of the present invention;

FIG. 7 is a fragmentary sectional view of the catheter of FIG. 6;

FIG. 8 is a sectional view of a connection member of the catheter;

FIG. 9 is a sectional view taken substantially as indicated along the line 9—9 of FIG. 8; and FIG. 10 is an elevational view, taken partly in section, of an inflation valve.

DESCRIPTION OF THE PREFERRED EMBODIMENTS

Referring now to FIG. 1, there is shown a kidney K of a patient having a renal calyces C forming a cavity in the kidney K. Referring to FIG. 2, there is shown a hollow needle 20 having a sharp distal tip 22, and a proximal hub 24. Referring to FIG. 3, there is shown a guide wire 26 of flexible material having a distal end 28, and a proximal end 30. Referring to FIG. 4, there is shown a stylet 32 having a rigid hollow tube 34. The tube 34 has a distal end 36, and a proximal end 38. The stylet 32 has a flexible plastic tubular section 40 secured over the proximal end 38 of the tube 34. Referring to FIG. 5, there is shown a scope 42 having an outer hollow sheath 44, and an inner optic telescope 46 removably received within the sheath 44.

Referring to FIGS. 6 and 7, there is shown a catheter 48 of the present invention. The catheter 48 has an elongated elastic shaft 50 having a distal end 52, a proximal end 54, and a drainage lumen 56 extending therethrough. The shaft 50 has an opening 58 extending through a wall of the shaft 50 and communicating with the drainage lumen 56 adjacent the proximal end 54 of the shaft 50 for a purpose which will be described below. The catheter 48 has an elastic sleeve 60 bonded to a distal portion of the shaft 50 in circumferential zones 62 and 64, such that the sleeve 60 defines a cavity 66 beneath the sleeve 60. The shaft 50 has an inflation lumen 68 extending through a wall of the shaft 50 with one end communicating with the cavity 66, and the other end extending completely to the proximal end 54 of the shaft 50.

The catheter 48 has a formed tip 70 having a distal opening 72 extending through the tip 70 and communicating with the drainage lumen 56. The tip 70 also has a plurality of drainage eyes 74 intermediate the opening 72 and a proximal end of the tip 70 and communicating with the drainage lumen 56.

The catheter 48 has a connector 76 removably received in the opening 58 in sealing relationship, such that the hollow connector 76 communicates with the drainage lumen 56. In a preferred form, the connector 76 has a hollow elastic plastic proximal portion 78, and a hollow rigid metal distal portion 80 removably received in the opening 58 of the shaft 50.

The catheter 48 has an inflation valve 82 of relatively small diameter and of known type which actuates by contact of a tip of a syringe, with the valve 82 being secured to the proximal end 54 of the shaft 50. The catheter 48 has means for establishing communication between the valve 82 and the proximal end of the inflation lumen 68.

With reference to FIGS. 7–10, the establishing means comprises a connector member 84. The connector member 84 has a distal plug 86 received in a proximal portion of the drainage lumen 56, such that the plug 86 seals the proximal portion of the drainage lumen 56. The connector member 84 has an annular flange 88 surrounding and being spaced from the plug 86, with the flange 88 abutting against the proximal end 54 of the shaft 50, and with the flange 88 and plug 86 defining an annular groove 90 communicating with a proximal end of the inflation lumen 68. As shown, the valve 82 has a hollow distal boss 92 communicating with the valve 82. The connector member 84 has a proximal recess 94 to receive the boss 92. Also, the connector member 84 has a plurality of inner spokes 96 defining apertures 98 between the spokes 96 and communicating between the boss 92 and the groove 90. In this manner, communication is established between the valve 82 and the proximal end of the inflation lumen 68 in order to inflate the sleeve 60.

In use, the needle 20 is passed under radiologic vision through the patient's body until the tip 22 is located in the renal calyces to obtain access to the kidney chamber. With the needle 20 in place, the guide wire 26 is passed through the needle 20, and the needle 20 is removed with the guide wire 26 in place to establish a path to the kidney K. Next, a plurality of dilators are inserted over the guide wire 26 in order to increase the size of the path to the kidney, and the dilators are then removed.

Next, the stylet 32 is inserted through the connector 76 and drainage lumen 56 until the distal end 36 of the stylet 32 contacts the tip 70. The guide wire 26 is received through the opening 72 of the tip 70 and through the hollow stylet 32, and the catheter 48 and stylet 32 are passed over the guide wire 26 until a distal portion of the catheter 48 is located in the renal calyces C. During this time, the stylet 32 supplies rigidity to the catheter 48 in order to facilitate the insertion procedure. Next, the tip of a syringe is utilized to actuate the valve 82, and the syringe is pumped to eject fluid through the valve 82, connector member 84 and the inflation lumen 68 to inflate the sleeve 60 in the renal calyces. The stylet 32 is then removed from the catheter 48. Finally, the proximal portion 78 of the connector 76 is connected to an upstream end of a drainage tube which is connected to a drainage bag, and urine drains through the catheter 48, the connector 76 and drainage tube into the bag in order to retain urine therein.

The scope 42 is utilized by the physician during the procedure in the event that he wishes to view the inside of the kidney K. In this event, the connector 76 is removed from the catheter shaft 50, and the sheath 44 is inserted over the valve 82 and the shaft 50 toward the kidney K. The sleeve 60 is then deflated through use of a syringe, and the catheter 48 is renoved from the sheath 44. Finally, the telescope 46 is inserted through the sheath 44 in order to view the inside of the kidney K. During this time, the catheter 48 facilitates the insertion procedure, since it is unnecessary to redefine the tract to the kidney K.

Once the viewing of the kidney K has been completed, the telescope 46 is removed from the sheath 44. Next, the catheter 48 is inserted through the sheath 44, and the sleeve 60 is inflated in the renal calyces C. The sheath 44 is removed over the catheter shaft 50 and valve 82, and the connector 76 is again attached to the opening 58 of the shaft 50 in order to resume the drainage procedure.

The foregoing detailed description is given for clearness of understanding only, and no unnecessary limitations should be understood therefrom, as modifications will be obvious to those skilled in the art.

What is claimed is:

1. A nephrostomy catheter, comprising:
   an elongated shaft having a drainage lumen extending through the shaft, a proximal end, an inflation lumen extending through a wall of the shaft, and an opening extending through the wall of the shaft at a location spaced distal from the proximal end of the shaft and communicating with the draingage lumen adjacent a proximal end of the shaft;
   an elastic sleeve secured to a distal portion of the shaft in circumferential zones, with the sleeve defining a cavity communicating with the inflation lumen;
   a connector removably received in sealing relationship in said opening with the connector communicating with the drainage lumen and extending to one side of the shaft;
   an inflation valve secured to the proximal end of the shaft and generally aligned with the shaft; and
   means for establishing communication between the valve and the inflation lumen wherein the establishing means comprises, a connector member having a distal plug received in a proximal portion of the drainage lumen, an annular flange surrounding and spaced from the plug, with the flange abutting against the proximal end of the shaft, and with the flange and plug defining an annular groove communicating with the inflation lumen.

2. The catheter of claim 1 wherein the connector has a hollow elastic proximal portion, and a hollow rigid distal portion received in the opening.

3. A nephrostomy catheter, comprising:
   an elongated shaft having a drainage lumen extending through the shaft, an inflation lumen extending through a wall of the shaft, and an opening extending through the wall of the shaft and communicating with the drainage lumen adjacent a proximal end of the shaft;
   an elastic sleeve secured to a distal portion of the shaft in circumferential zones, with the sleeve defining a cavity communicating with the inflation lumen;
   a connector removably received in sealing relationship in said opening with the connector communicating with the drainage lumen;
   an inflation valve secured to the proximal end of the shaft; and
   means for establishing communication between the valve and the inflation lumen wherein the establishing means comprises, a connector member having a distal plug received in a proximal portion of the drainage lumen, an annular flange surrounding and spaced from the plug, with the flange abutting against the proximal end of the shaft, and with the flange and plug defining an annular groove communicating with the inflation lumen, and wherein the valve has a hollow distal boss communicating with the valve, and the connector member has a proximal recess to receive the boss, and a plurality of inner spokes defining apertures between the spokes communicating between the boss and groove.

* * * * *